United States Patent [19]

Voss et al.

[11] Patent Number: 5,942,200

[45] Date of Patent: *Aug. 24, 1999

[54] METHOD FOR REMOVING CARBON OXIDES FROM A HYDROGEN STREAM

[75] Inventors: Andrew P. Voss, Cerritos; Michael J. Pedersen, Irvine, both of Calif.

[73] Assignee: Atlantic Richfield Company, Los Angeles, Calif.

[ * ] Notice: This patent is subject to a terminal disclaimer.

[21] Appl. No.: 09/022,928

[22] Filed: Feb. 12, 1998

Related U.S. Application Data

[63] Continuation-in-part of application No. 08/732,823, Oct. 15, 1996, Pat. No. 5,770,781, and a continuation-in-part of application No. 08/732,828, Oct. 15, 1996, Pat. No. 5,773,675.

[51] Int. Cl.$^6$ ............................... C01B 17/16; B01J 8/00
[52] U.S. Cl. ........................................... 423/230; 423/247
[58] Field of Search .................................. 423/220, 230, 423/246, 247

[56] References Cited

U.S. PATENT DOCUMENTS

| | | | |
|---|---|---|---|
| 5,770,781 | 6/1998 | Voss et al. ............................. | 585/253 |
| 5,773,675 | 6/1998 | Voss et al. ............................. | 585/304 |

OTHER PUBLICATIONS

R. Kramer, M. Fishbacher and H. L. Gruber, "Slow Uptake of Oxygen and Carbon Monoxide by Platinum/Silica (Europt–1) and Subsequent Effects on Hydrogenation of Benzene and Hydrogenolysis of Methylcyclopenatane", Applied Catalysis, 42 (1988) 337–350, Elsevier Science Publishers B.V., Amsterdam—Printed in The Netherlands.

Geltramini, "Catalytic Naphtha Reforming", edited by G.J. Antos, et al; Mar., 1995, Dekket, Inc., pp. 314–315.

Rylander, Paul Nels, "Catalytic Hydrogenation over Platinum Metals", New York, Academic Press, 1967, p. 20.

"IFP Process Literature" (Sales Material generally available to Refiners).

"Setting the Pace with IFP for the 21st Century", Jun. 1994 (Promotional Literature from IFP that is generally available to refiners).

Schmidt, R.J., Weiszmann, J.A., and Johnson, J.A., "Catalysts—key to low–cost isomerization", Oil & Gas Journal, May 27, 1985, pp. 80–88.

Schmidt, R.J., Johnson, J.A., Hibbs, F.M. and Froggatt, M.D., "Two New Catalysts for Isomerization of Light Straight Run Naphtha", For Presentation at the Fourth Scientific Conference, Scientific Research Council, Baghdad, Iraq, Oct. 23–28, 1986.

Johnson, J.A., Hobbs, S.H., Wheeler, T., "UOP PENEX Technology—A Flexible Solution", May 5, 1986.

"Section 11 Isomerization", Modern Refinery Operations & Practices, Hydrocarbon Publishing Co., 1993, pp. 94–97.

Reno, M.E., Haizmann, R.S., Johnson, B.H., Kuchar, P.J., Piotrowski, P.P. and Zarchy, A.S., "Improved Profits with Paraffin Isomerization Innovations", 1990 UOP, Des Plaines, Illinois.

Symoniak, M.F. and Holcombe, T.C., "Total Isomerization Gains Flexibility", Hydrocarbon Processing, May 1983, pp. 62–64.

"Isomerization", Hydrocarbon Processing, Nov. 1990, p. 122.

Schmidt, R.J. and Weiszmann, J.A., "Low Cost Options for Upgrading Light Straight Run Naphtha", American Petroleum Institute, 1985, 30 pp.

"Applications for Isomerization Processes", ICI Puraspec Processes, ICI Katalco, Two TransAm Plaza Drive, Oakbrook Terrace, Illinois 60181, 1993, 6 pp.

Lietz, G., and Volter, J., "Catalytic Hydrogenation of Methylbenzenes on Platinum," Symposium on the Mechanisms of Hydrocarbon Reactions Jun. 5–7, 1973, Siofok, Hungary, pp. 151–161.

Hibbs, F.M., "New Technologies for Efficient Refining in the Environmentally Conscious 1990s", Petroleum Review, May 1994, pp. 210–213.

Isomerization Definition from "Chemical and Process Technology Encyclopedia", Douglas M. Considine, Editor, McGraw–Hill Book Company, 1974, pp. 662–665.

Primary Examiner—Glenn Caldarola
Assistant Examiner—In Suk Bullock
Attorney, Agent, or Firm—F. Lindsey Scott

[57] ABSTRACT

A method for removing carbon oxides from a hydrogen stream containing more than 0.1 ppmv of carbon monoxide, carbon dioxide or a mixture thereof, by charging the hydrogen with a hydrocarbonaceous stream containing a minor amount of aromatics to an aromatics saturation zone; saturating at least a portion of the aromatics and methanating at least a major portion of the carbon oxide to produce a reduced aromatics content hydrocarbonaceous stream and a reduced carbon oxide content hydrogen stream; and recovering the reduced aromatics content hydrocarbonaceous stream and the reduced carbon oxide content hydrogen stream. The hydrogen may optionally be dried or further purified.

16 Claims, 3 Drawing Sheets

METHOD FOR REMOVING CARBON OXIDES FROM A HYDROGEN STREAM

CROSS-REFERENCE TO RELATED APPLICATIONS

This application is a continuation-in-part of U.S. Ser. No. 08/732,823, now U.S. Pat. No. 5,770,781, entitled "A Method for Eliminating Carbon Oxides in Feeds To a $C_5$ and $C_6$ Paraffin Isomerization Process" filed Oct. 15, 1996 by Andrew P. Voss and Michael J. Pedersen and U.S. Ser. No. 08/732,828, now U.S. Pat. No. 5,773,675, entitled "A Method for Eliminating Carbon Oxides in the Hydrogen Feed to a Butane Isomerization Process" filed Oct. 15, 1996 by Andrew P. Voss and Michael J. Pedersen.

BACKGROUND OF THE INVENTION

1. Field of the Invention

This invention relates to a method for removing carbon oxides from a hydrogen stream by treatment of the hydrogen stream in an aromatics saturation reactor.

2. Description of Related Art

In refinery processes it is desirable that a substantial portion of the crude oil or other petroleum feed stock to the refinery be converted to gasoline range materials. Gasoline comprises a hydrocarbon fraction generally having a boiling range of about 30 to about 430° F. and a research octane number (RON) of at least about 90. A variety of refinery processes are used to increase the gasoline yield from crude oil charged to a refinery. Such processes include catalytic cracking, reforming, alkylation and the like. In the refining process naphthenic and paraffinic hydrocarbons are produced which are of a suitable boiling range for use as gasoline but which have an octane rating too low for use as gasoline. The octane rating of such hydrocarbons is typically increased by reforming. In the reforming process, the naphthene hydrocarbons and paraffin hydrocarbons are converted to aromatic hydrocarbons. As is well known to those skilled in the art, aromatic materials have a higher octane rating than similar boiling range paraffinic or naphthenic materials.

While such reforming processes are effective to produce higher octane rating materials, the materials so produced are aromatic and in recent years there have been requirements to reduce the aromatic component content of gasoline and other fuels. While reforming remains a valuable tool for increasing the octane rating of paraffinic hydrocarbons increased attention has been directed to other methods for increasing the octane rating of paraffinic hydrocarbons.

One such method is the use of isomerization. Isomerization of gasoline range paraffins is frequently used with paraffinic hydrocarbons containing from 5 to 6 carbon atoms. Such $C_5/C_6$ streams are frequently subjected to benzene saturation and isomerization treatment to saturate benzene and other aromatics which may be present in minor amounts (herein benzene) with the $C_5$ and $C_6$ paraffins and convert straight chain $C_5$ and $C_6$ paraffinic hydrocarbons to branched chain, or isomerized, $C_5$ and $C_6$ paraffins which have a higher octane rating than the corresponding straight chain paraffins. One such method is disclosed in co-pending U.S. Ser. No. 08/732,823 entitled "A Method for Eliminating Carbon Oxides in Feeds To a $C_5$ and $C_6$ Paraffin Isomerization Process".

Such isomerization processes are well known to those skilled in the art as discussed in *Chemical and Process Technology Encyclopedia*, Douglas M. Considine, Ed., McGraw Hill Book Company, 1974, pp. 662–665. As discussed in this reference it is a common practice to also isomerize $C_4$ hydrocarbons for use in alkylation processes and the like. One such method is disclosed in co-pending U.S. Ser. No. 08/732,828 entitled "A Method for Eliminating Carbon Oxides in the Hydrogen Feed to a Butane Isomerization Process". It is also noted that moisture must be minimized in the isomerization zone and that the amount of benzene in the paraffin feed stock should be minimized. It is also known to those skilled in the art that carbon oxides, even in small amounts, in the feed stream are extremely detrimental to the isomerization catalyst. Such carbon oxides are methanated over the isomerization catalyst. The methanation reaction produces water which permanently poisons the isomerization catalyst. Accordingly it has long been recognized that carbon oxides in the feed to the isomerization reactor must be minimized and desirably maintained at levels below 0.1 part per million by volume (ppmv). Various other refinery and chemical plant processes, such as processes catalyzed by organo metallic catalysts, such as alpha olefin polymerization processes and other processes catalyzed by catalysts which are sensitive to carbon oxides or water, require hydrogen containing very low amounts or no carbon oxides.

It has also been recognized that the presence of benzene and any other aromatics present in the paraffin feed to the isomerization reactor is detrimental since the benzene and other aromatics are hydrogenated over the isomerization catalyst causing an increase in reactor temperature which promotes unwanted cracking reactions and increased hydrogen consumption. Thus it is desirable to hydrogenate benzene and any other aromatics in the paraffin feed before the isomerization reaction zone in a unit such as a benzene saturation reactor.

Benzene saturation units have long been known to those skilled in the art and are used to saturate benzene and other aromatic compounds in such paraffinic streams. Such processes typically use a catalyst comprising from about 0.1 to about 1.0 weight percent platinum on a suitable catalyst support such as alumina or silica alumina. Such units typically operate at an inlet temperature from about 325 to about 800° F. and a pressure from about 200 to about 700 pounds per square inch gauge (psig). Since carbon oxides temporarily poison the catalyst in the benzene saturation reactor it has been considered necessary to maintain the carbon oxide content of the streams charged to the benzene saturation reactor at low levels.

In recent years there has been increased interest in removing benzene and other aromatic components from $C_5/C_6$ paraffinic streams and isomerizing $C_5/C_6$ paraffinic streams because of the increased emphasis on the production of gasoline having a reduced aromatics content. Accordingly, improved methods have been sought for producing such gasolines from existing refinery streams.

Similar catalysts are used in aromatics saturation units for the treatment of other hydrocarbonaceous streams to reduce the amount of aromatics in such streams. Some such processes are solvent treating to saturate aromatics in naphtha streams, cyclohexane hydrogenation, lube oil hydrogenation and the like. The catalysts used in such units are frequently similar to those described above for the benzene saturation unit, although other catalysts known to the art for aromatics saturation may be used, and it has been considered necessary to maintain the carbon oxide content of the streams charged to the aromatics saturation reactor at low levels. The reaction conditions in such units are generally similar to the reaction conditions in the benzene saturation unit, except for lube oil hydrogenation which is typically at a higher pressure, and lower space velocity. Such hydrocarbonaceous streams may have a higher aromatics content than the paraffinic stream and the aromatics are typically present in the hydrocarbonaceous stream in minor amounts which may be up to about 30 volume percent or higher. The operation of such aromatics saturation units to saturate aromatics is well-known to those skilled in the art.

In many refineries the available hydrogen sources contain amounts of carbon monoxide, carbon dioxide or mixtures thereof up to as much as about 200 ppmv. Accordingly, in the past such hydrogen streams have been passed through a methanation reactor to react the carbon oxides to produce water and methane with the resulting water being removed prior to charging the hydrogen to isomerization reactors or other processes requiring carbon oxide-free hydrogen. Similarly, the carbon oxides and water have been removed prior to using such hydrogen streams in benzene saturation and aromatics saturation reactors.

Accordingly, an improved method has been sought for reducing the capital cost of such processes for producing hydrogen streams containing substantially no carbon oxides.

SUMMARY OF THE INVENTION

According to the present invention, carbon oxides are removed from a hydrogen stream containing at least one carbon oxide selected from the group consisting of carbon monoxide and carbon dioxide by charging the hydrogen stream to an aromatics saturation zone wherein a hydrocarbonaceous stream containing a minor amount of aromatic compounds is treated to saturate at least a portion of the aromatic compounds and methanate at least a major portion of the carbon oxides in the presence of an aromatics saturation catalyst at aromatics saturation conditions to produce a reduced aromatics content hydrocarbonaceous stream and a reduced carbon oxide content hydrogen stream.

According to a further embodiment of the present invention, carbon oxides are removed from a hydrogen stream containing at least one carbon oxide selected from the group consisting of carbon monoxide and carbon dioxide by: charging the hydrogen stream to a benzene saturation zone wherein a paraffinic stream containing benzene and at least 50 volume percent $C_5$ and $C_6$ paraffins is treated to saturate at least a major portion of the benzene and methanate at least a major portion of the carbon oxides at a temperature from about 325 to about 800° F. and a pressure from about 200 to about 700 psig in the presence of a benzene saturation catalyst to produce a reduced benzene content paraffinic stream and a reduced carbon oxide content hydrogen stream; and separating the reduced benzene content paraffinic stream and the reduced carbon oxide content hydrogen stream to produce a reduced carbon oxide content hydrogen stream.

DESCRIPTION OF THE PREFERRED EMBODIMENTS

In the description of the Figures the same numbers will be used throughout to refer to the same or similar components. Various pumps, valves and the like necessary to achieve the indicated flows have not been shown except when necessary for the process flow description.

While the method of the present invention is useful with aromatics saturation reactors and reaction zones in general, it will be illustrated by reference to a benzene saturation unit for the saturation of benzene in a $C_5/C_6$ paraffinic stream.

Figure 1:
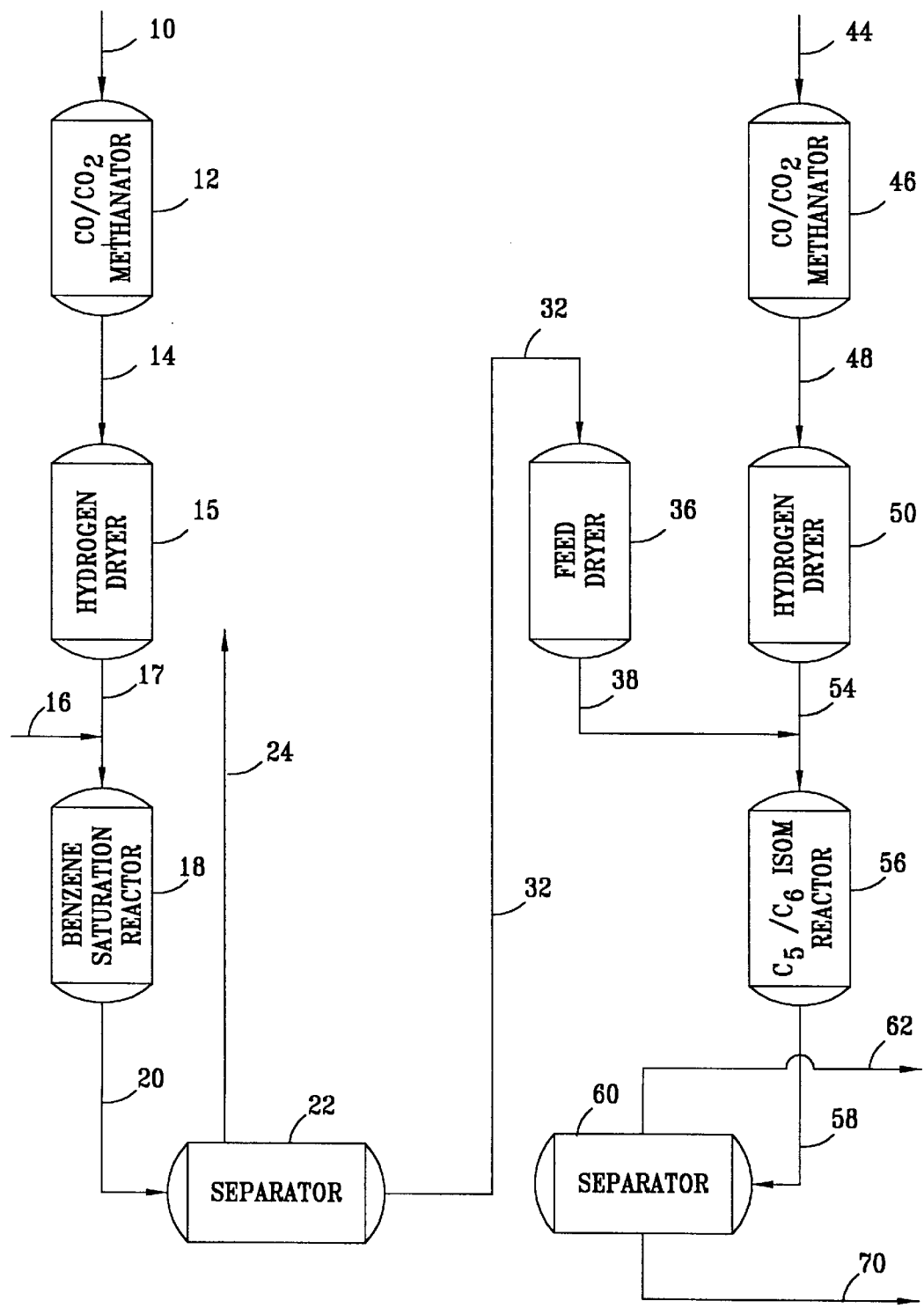
FIG. 1 is a schematic diagram of a prior art process wherein the benzene content of a predominantly $C_5$ and $C_6$ paraffin stream is reduced and wherein the reduced benzene content paraffin stream is isomerized to produce an isomerized paraffin stream.

In FIG. 1 a typical $C_5/C_6$ paraffin isomerization process is shown. A hydrogen line 10 supplies hydrogen containing more than 0.1 ppmv of at least one carbon oxide to a $CO/CO_2$ methanator 12 containing a suitable methanation catalyst which is typically a nickel-based catalyst. Methanation catalysts are considered to be well known to those skilled in the art as are methanation conditions. The resulting methanated stream containing hydrogen, methane and water passes through a line 14 to a hydrogen dryer 15 where water is removed. Hydrogen dryer 15 may be any suitable hydrogen drying system. The dried hydrogen then passes through a line 17 to a benzene saturation reactor 18. A paraffinic feed stream typically containing minor amounts (up to about 10 volume percent) of benzene and at least 50 volume percent paraffins containing from 5 to 6 carbon atoms (herein $C_5$ and $C_6$ paraffins) is fed through a line 16 and combined with the hydrogen in line 17 for charging to benzene saturation reactor 18. The reaction product comprising the paraffinic stream having a reduced benzene content and hydrogen is recovered through a line 20 and passed to a separator 22 where the hydrogen may be recovered through a line 24 and passed to discharge from the process. The hydrogen in line 24 will contain methane from CO/CO2 methanator 12 and possibly other light gases. The operation of benzene saturation processes is considered to be well known to those skilled in the art.

The paraffinic product recovered from separator 22, is passed through a line 32 to a feed dryer 36. Feed dryer 36 may be any suitable hydrocarbon drying system. The dried paraffin stream is then recovered through a line 38 and passed through line 38 to combination with hydrogen in a line 54 and charged to an isomerization reactor 56.

Hydrogen for isomerization reactor 56 is supplied through a line 44 and as supplied includes more than 0.1 ppmv of at least one carbon oxide. The hydrogen is passed through line 44 to a CO/CO2 methanator 46 where the carbon oxides are converted to methane and water. The resulting product stream is then passed through a line 48 to a hydrogen dryer 50 where water is removed by the use of any suitable hydrogen drying process. The dried hydrogen is passed through line 54 to isomerization reactor 56 in combination with the paraffinic feed stream from line 38.

The resulting reaction product comprising isomerized $C_5$ and $C_6$ paraffins and hydrogen is recovered through a line 58 and passed to a separator 60. In separator 60 the isomerized paraffin product is recovered through a line 70 and passed to use as a blending component of gasoline or the like. The recovered hydrogen, including methane and possibly other light hydrocarbons, is recovered through a line 62 and passed to discharge from the process.

The operation of benzene saturation processes and isomerization processes as described above is well known to those skilled in the art. In the benzene saturation reactor 18 a catalyst comprising from about 0.1 to about 1.0 weight percent platinum on alumina, aluminosilicate or the like may be used as a catalyst at a temperature typically from about 325 to about 800° F. and a pressure typically from about 200 to about 700 psig. The paraffin stream space velocity in benzene saturation reactor 18 is typically from about 2 to about 10 liquid hourly space velocity (LHSV). Liquid Hourly Space Velocity is defined as the volume of liquid feed per unit volume of catalyst per hour. The operating temperature is limited by the upper operating temperature limits of the catalyst and reactor and may limit the amount of benzene which may be included in the charge to the reactor. The operating temperature is also limited by the chemical equilibrium of the benzene hydrogenation reaction which is not favorable above 800° F.

Catalysts of a similar type, and other catalysts commonly used to saturate aromatics which are similarly sensitive to carbon oxides in the hydrogen stream, are used to saturate aromatics in other streams as well. The specific catalysts and reaction conditions are well-known to those skilled in the art. Some such processes are solvent treating to saturate aromatics in naphtha streams, cyclohexane hydrogenation, lube oil hydrogenation and the like.

Suitable isomerization catalysts include supported platinum group metal catalysts which may comprise from about 0.1 to about 2.0 weight percent platinum group metal component supported on activated alumina, crystalline aluminosilicate or other suitable support materials. The catalyst may also contain rhodium group metal components as well as promoters. Such catalysts may contain up to 20 weight percent acidic chloride components and are generally considered to be highly acidic catalysts. Such catalysts are considered to be known to the art.

The mixture of hydrogen and feed stock is typically charged to the isomerization reactor at a temperature from about 250 to about 600° F. and a pressure from about 100 to about 600 psig. The hydrogen is desirably supplied to such isomerization processes in an amount equal to about 500 to about 4,000 standard cubic feet per barrel of $C_5/C_6$ paraffin feed stock. The LHSV in isomerization reactor 56 is typically from about 1 to about 4.

Such process variations are considered to be well known to those skilled in the art.

Figure 2:
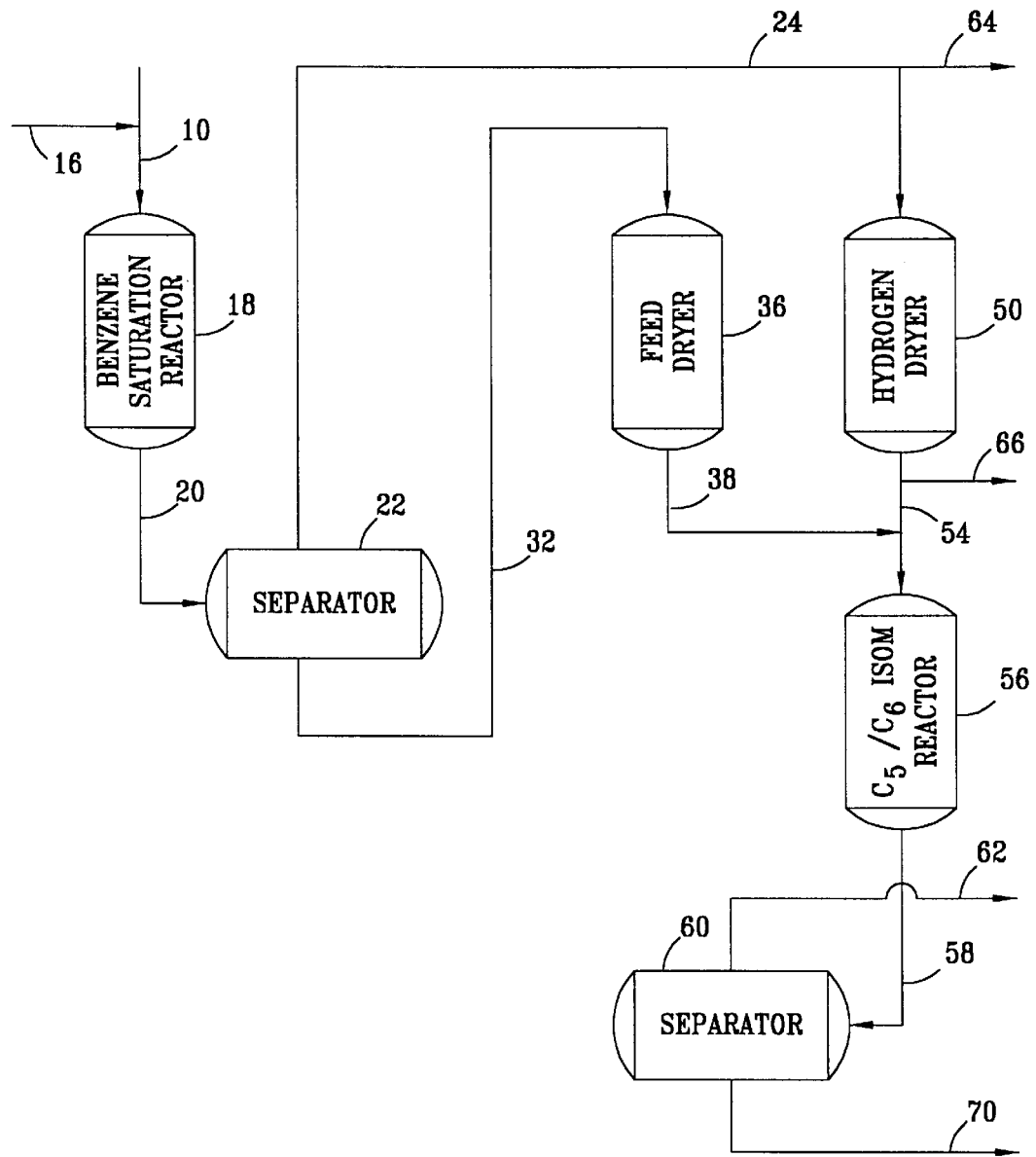
FIG. 2 is a schematic diagram of an embodiment of the present invention.

In FIG. 2 a process according to the present invention is shown. A hydrogen stream containing up to about 200 ppmv of carbon monoxide, carbon dioxide or mixtures thereof is charged to benzene saturation reactor 18 through a line 10 in mixture with a paraffin stream containing at least 50 volume percent $C_5$ and $C_6$ paraffins and minor amounts (up to about 10 volume percent) of benzene which is charged through line 16 to reactor 18. The resulting product is passed through line 20 to a separator 22 from which a hydrogen stream containing methane, water and hydrogen is recovered and passed through line 24 to hydrogen dryer 50 from which dried hydrogen containing methane is recovered through line 54 and passed to $C_5/C_6$ isomerization reactor 56. The reduced benzene paraffinic stream is recovered through line 32 and passed to feed dryer 36 and from feed dryer 36 through line 38 to line 54. Isomerization reactor 56 operates as discussed previously to produce an isomerized paraffinic stream 70 with the hydrogen being discharged from the process through line 62.

It has been discovered by the applicants that the benzene saturation and aromatics saturation reactors can tolerate substantial quantities, i.e. up to at least about 200 ppmv of carbon monoxide, carbon dioxide or mixtures thereof in a hydrogen stream without inhibiting the aromatics saturation catalyst to the extent that the aromatics saturation reaction is adversely affected. While carbon oxides are known to temporarily poison and inhibit the functioning of aromatics saturation catalysts it has been found that this damage is not significant when less than about 200 ppmv of carbon oxides are present in the hydrogen charged to aromatics saturation reactors such as benzene saturation reactor 18. In the practice of the process described above sufficient hydrogen is charged to benzene saturation reactor 18 so that hydrogen is available in sufficient quantities to flow in series through benzene saturation reactor 18 and isomerization reactor 56 to provide dried hydrogen from which carbon oxides have been removed for use in isomerization reactor 56 in the quantities required plus additional dried hydrogen from which carbon oxides have been removed for use in other processes and the like. The additional dried hydrogen is recovered via a line 64 if no drying is required and from a line 66 if the hydrogen is dried. The additional hydrogen is optionally dried and may optionally be treated by membrane separation processes or other processes known to the art to remove methane or other contaminants as known to those skilled in the art by membrane separation, adsorption or the like processes. The stream discharged from the isomerization reactor may be used as a carbon oxide free hydrogen stream or passed to further treatment as noted above. Carbon oxide-free hydrogen may also be produced in a similar manner from other aromatics saturation processes.

In the process of the present invention the requirement for methanation vessels for each process or at least one methanation vessel to supply hydrogen to the two processes has been eliminated. This is a significant process simplification leading to capital and operating cost savings. As noted previously, the benzene or other aromatics saturation catalyst can tolerate up to 200 ppmv of carbon oxides in a hydrogen stream without detriment to the aromatics saturation reaction. These carbon oxides are methanated over the benzene saturation catalyst to produce methane and water. Any carbon oxides present in the $C_5/C_6$ paraffin stream are also methanated in the benzene saturation reactor. The water is subsequently removed in hydrogen dryers 36 and 50 and the methane is not detrimental to the isomerization reactions in isomerization reactor 56.

The paraffinic stream charged to benzene saturation reactor 18 and subsequently to isomerization reactor 56 comprises primarily $C_5/C_6$ paraffinic hydrocarbons. Hydrocarbons containing seven or more carbon atoms tend to crack in the isomerization reaction zone thereby producing undesirable carbon deposits on the catalyst and $C_4$ paraffins are generally isomerized in a separate process and used for other purposes. Benzene is saturated in the benzene saturation reactor.

Figure 3:
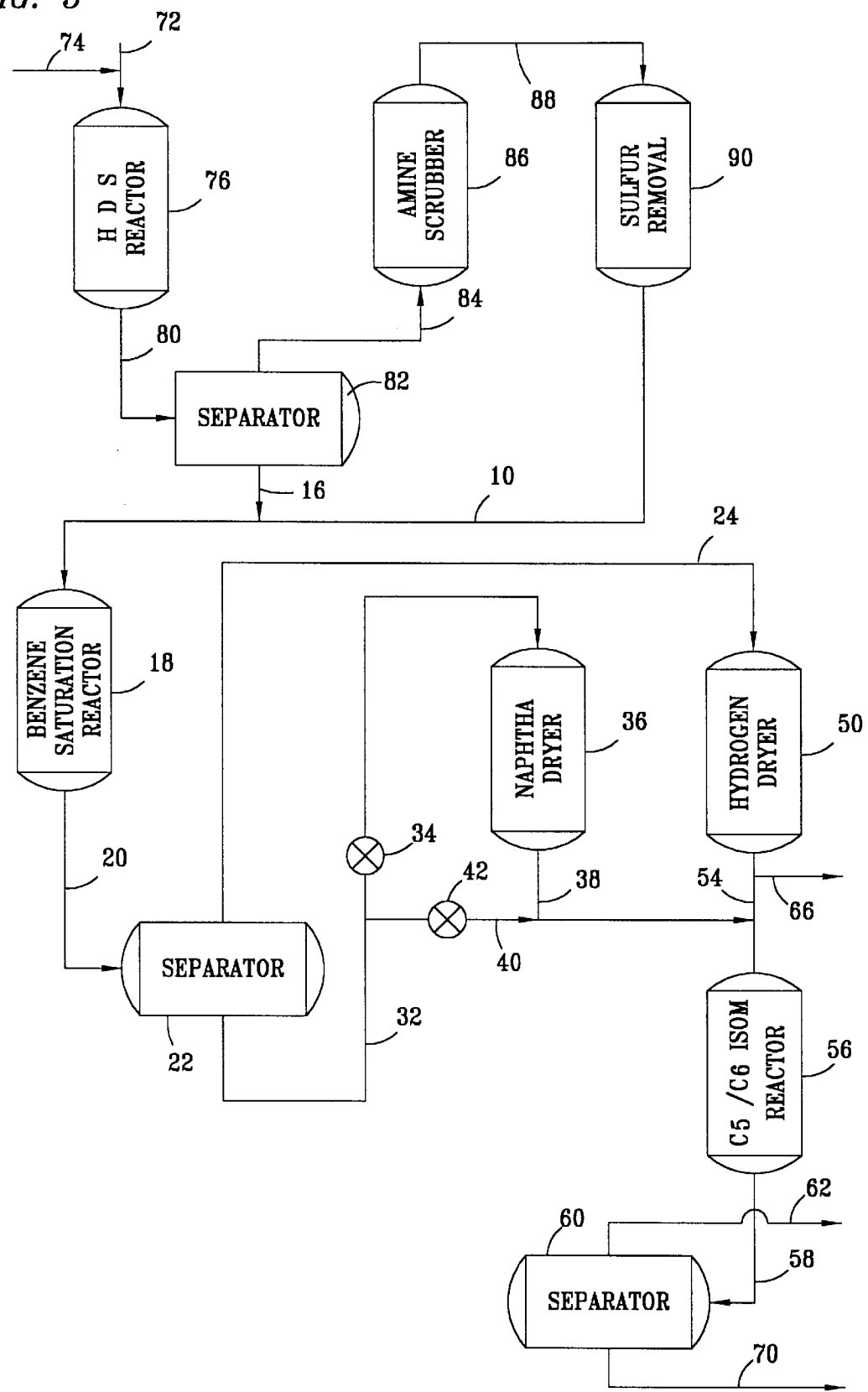
FIG. 3 is a schematic diagram of a further embodiment of the method of the present invention.

In FIG. 3 a variation of the process of the present invention is shown wherein a $C_5/C_6$ paraffinic feed stream which may contain carbon oxides is charged through a line 74 and combined with hydrogen that may contain carbon oxides supplied through a line 72 with the result that the combined stream may contain carbon oxides. The combined stream is passed to a hydrodesulfurization (HDS) reactor 76. Reactor 76 is a typical hydrodesulfurization reactor as known to those skilled in the art wherein sulfur compounds contained in a naphtha paraffinic stream are converted to hydrogen sulfide and recovered with the paraffinic stream through a line 80. The product stream is separated in a separator 82 into a paraffinic stream which is recovered via a line 16 and a hydrogen stream containing the hydrogen sulfide and carbon oxides which is passed via a line 84 to a first hydrogen sulfide removal unit such as an amine, e.g. diethanolamine (DEA), scrubber 86 where hydrogen sulfide and some carbon dioxide are removed with the resulting hydrogen stream being passed through a line 88 to a second sulfur removal section 90 such as a zinc oxide sulfur absorber bed. The desulfurized hydrogen is then passed to benzene saturation reactor 18 through a line 10. The remaining portion of the process functions as described in the discussion of FIG. 2.

In many instances hydrogen available in refinery operations contains small amounts of carbon oxides. Such carbon oxides can be detrimental to the benzene or other aromatics saturation catalyst at high concentrations because of competitive adsorption. They are particularly detrimental and result in permanent deactivation of the isomerization reactor catalyst because of water produced from the methanation reaction. It is very desirable that carbon oxide-free hydrogen streams be available for use in isomerization processes, alpha olefin polymerization processes and other processes using organo-metallic catalysts and other processes requiring carbon oxcide-free hydrogen. According to the present invention carbon oxides are readily removed from such hydrogen streams in benzene and aromatics saturation processes with no detriment to either process. While the carbon oxides tend to temporarily deactivate the benzene or aromatics saturation catalyst to a slight extent the deactivation is insufficient to inhibit the functioning of the catalyst for benzene or aromatics saturation. Since the deactivation is temporary, the slight amount of deactivation caused by the presence of the carbon oxides in the hydrogen charged to the aromatics saturation reactor does not result in sufficient cumulative detriment to the aromatics saturation catalyst to prevent the effective saturation of aromatics. The resulting carbon oxide-free hydrogen stream is then dried to remove the water and used in processes requiring carbon oxide-free and water-free hydrogen. The process of the present invention has thus resulted in the treatment of a hydrogen stream to remove undesirable carbon oxides at a point in the process where their removal is not detrimental to the function of the process to produce the clean carbon oxide-free hydrogen required for use in processes requiring carbon oxide-free hydrogen. The process of the present invention does not require a separate methanation reactor for carbon oxide removal. The hydrocarbonaceous streams charged to the aromatics saturation reactors will normally be reasonably dry but, in the event that water beyond the tolerance level of the aromatics saturation catalyst is present, these streams may require drying. Such process requirements are well known to those skilled in the art. The amounts of additional hydrogen which can be charged to the aromatics saturation reactor is limited primarily by the vessel capacity, metallurgy and process equipment hydraulics.

Having thus described the present invention by reference to certain of its preferred embodiments it is pointed out that the embodiments described are illustrative rather than limiting in nature and that many variations and modifications are possible within the scope of the present invention. Such variations and modifications may be considered obvious and desirable by those skilled in the art based upon the foregoing description of preferred embodiments.

Having thus described the invention we claim:

1. A method for removing carbon oxides from a hydrogen stream containing at least one carbon oxide selected from the group consisting of carbon monoxide and carbon dioxide, the method consisting essentially of:

a) charging the hydrogen stream to a aromatics saturation zone wherein a hydrocarbonaceous stream containing aromatic compounds is treated to saturate at least a portion of the aromatic compounds and methanate at least a major portion of the carbon oxides in the presence of an aromatics saturation catalyst to produce a reduced aromatics content hydrocarbonaceous stream and a reduced carbon oxide content hydrogen stream;

b) separating the reduced aromatic content hydrocarbonaceous stream and the reduced carbon oxide content hydrogen stream to produce a reduced carbon oxide content stream.

2. The method of claim 1 wherein the hydrocarbonaceous stream is a lube oil stream.

3. The method of claim 1 wherein the hydrocarbonaceous stream is a naphtha stream.

4. The method of claim 1 wherein the hydrocarbonaceous stream is a cyclohexane stream.

5. The method of claim 1 wherein the hydrocarbonaceous stream contains up to about 30 volume percent aromatics.

6. The method of claim 1 wherein the reduced carbon oxide content hydrogen contains less than 0.1 ppmv carbon oxide.

7. The method of claim 1 wherein the hydrogen stream containing carbon oxides contains up to about 200 ppmv carbon oxides.

8. The method of claim 1 wherein the aromatics saturation catalyst comprises from about 0.1 to about 1.0 weight percent platinum supported on alumina.

9. The method of claim 1 wherein at least a portion of the reduced carbon oxide content hydrogen is dried.

10. The method of claim 1 wherein at least a portion of the reduced carbon oxide content hydrogen is further purified.

11. A method for removing carbon oxides from a hydrogen stream containing at least one carbon oxide selected from the group consisting of carbon monoxide and carbon dioxide, the method consisting essentially of:

a) charging the hydrogen stream to a benzene saturation zone wherein a paraffinic stream containing benzene and at least 50 percent $C_5$ and $C_6$ paraffins is treated to saturate at least a major portion of the benzene and methanating at least a major portion of the carbon oxides at a temperature from about 325 to about 800° F. and a pressure from about 200 to about 700 psig in the presence of a benzene saturation catalyst to produce a reduced benzene content paraffinic stream and a reduced carbon oxide content hydrogen stream; and, b) separating the reduced benzene content paraffinic stream and the reduced carbon oxide content hydrogen stream to produce a reduced carbon oxide content hydrogen stream.

12. The method of claim 11 wherein the reduced carbon oxide content hydrogen stream contains less than about 0.1 ppmv carbon oxide.

13. The method of claim 11 wherein the hydrogen stream contains less than about 200 ppmv of at least one carbon oxide.

14. The method of claim 11 wherein the benzene saturation catalyst comprises from about 0.1 to about 1.0 weight percent platinum supported on alumina.

15. The method of claim 11 wherein the liquid hourly space velocity of the paraffinic stream in the benzene saturation reactor is from about 2 to about 10.

16. The method of claim 11 wherein at least a portion of the reduced carbon oxide content hydrogen stream is dried.

\* \* \* \* \*